United States Patent

Neti et al.

[11] 4,078,981
[45] Mar. 14, 1978

[54] CO₂ INTERFERENCE FREE O₂ ELECTRODE
[75] Inventors: Radhakrishna M. Neti, Brea; Ray L. Roggenkamp, Redding, both of Calif.
[73] Assignee: Beckman Instruments, Inc., Fullerton, Calif.
[21] Appl. No.: 747,447
[22] Filed: Dec. 3, 1976
[51] Int. Cl.² ............................................. G01N 27/54
[52] U.S. Cl. ................................................ 204/195 P
[58] Field of Search ........................... 204/1 P, 195 P; 128/2 E, 2.1 E; 324/29

[56] References Cited
U.S. PATENT DOCUMENTS

| 3,196,100 | 7/1965 | Digby | 204/1 P X |
| 3,655,546 | 4/1972 | Marovich et al. | 204/195 P |
| 3,997,419 | 12/1976 | Scott et al. | 204/195 P |

Primary Examiner—G. L. Kaplan
Attorney, Agent, or Firm—R. J. Steinmeyer; P. R. Harder; D. A. Streck

[57] ABSTRACT

An improved electrode for use in oxygen determination is disclosed. Interference from carbon dioxide is eliminated by combining an improved electrolyte with means for permitting rapid electrolyte movement into and out of the space between the cathode and the membrane covering the cathode to maintain the pH of the electrolyte in the space substantially constant. The electrolyte consists of a KCl solution containing KOH of from 0.1 to 2%.

13 Claims, 5 Drawing Figures

$CO_2$ INTERFERENCE FREE $O_2$ ELECTRODE

BACKGROUND OF THE INVENTION

The present invention relates to electrodes capable of detecting a gas in a fluid and more particularly to electrodes capable of measuring the presence and the amount of oxygen.

One of the analytical methods of oxygen determination is the amperometric method. This method is quite rapid, simple in operation and is especially suited for determining either gaseous or dissolved oxygen in liquids. In the amperometric method, an electrode such as that shown in FIG. 1 is employed. In such an electrode, generally indicated as 10, body 12 is provided having an enclosure 14 therein containing means 16 for supporting a gold cathode 18. A membrane holder 20 and cap 22 are provided to hold a polymeric membrane material 24 such as polytetrafluoroethylene of a thickness as from 0.00025 inches to 0.002 inches stretched over the gold cathode 18 thereby completely enclosing enclosure 14. Enclosure 14 is then filled with an electrolyte 26, typically a 5% KCl solution, either buffered or unbuffered. Additionally, an anode 28, typically silver, is disposed within enclosure 14 in contact with electrolyte 26. A potential of 750 millivolts is applied between the anode 28 and the cathode 18 by means 29 connected thereto. In stretching the membrane 24 over cathode 18, a very minimal amount of electrolyte 26 is contained between gold cathode 18 and membrane 24. As a sample fluid is brought in contact with membrane 24, oxygen diffuses through membrane 24 to contact the gold cathode 18 in the presence of the electrolyte 26. A current flow results which is linear with the partial pressure of oxygen being sampled. Thus, this current can be measured and correlated to the amount of oxygen in the sample.

While this method is satisfactory in many applications, it suffers drastically in atmospheres of high $CO_2$ such as encountered in monitoring automobile exhaust or stack gas emissions. Such an electrode as that of FIG. 1, as described above, becomes less sensitive to $O_2$ upon even brief exposure to high concentrations of $CO_2$ and may take several hours to recover so as to indicate the proper value of $O_2$. The response of such an electrode is highly dependent on the pH of the electrolyte at the interface between the gas diffusing through the membrane and the cathode. At low, or acid, pH levels the response is low. At high, or base, pH levels the response is higher. Typical responses by a prior art electrode are shown in FIG. 2 and FIG. 3. In FIG. 2, the electrode was first exposed to ambient air containing approximately 21% $O_2$. It was then exposed to pure nitrogen. FIG. 2 shows the response which was both expected and achieved. Upon the exposure to $N_2$, the response dropped to the zero line. Upon exposure to air, the response climbed to the level indicating approximately 21% $O_2$. This cycle was repeatable without problem. Referring now to FIG. 3, the expected and actual response of a prior art electrode is shown when the electrode was exposed to ambient air and then exposed to a mixture of 15% $CO_2$ plus 3% $O_2$ and the balance nitrogen. When exposed to the moxture, the expected response is for the output to drop to the 3% level, being an indication of the 3% $O_2$ content of the mixture. Upon exposure to ambient air, it is expected that the output will climb to the 21% oxygen level of the ambient air. The actual response, however, was not as anticipated. When the electrode was exposed to the mixture, the response fell to the expected 3% $O_2$ level. When the electrode was subsequently exposed once again to the ambient air sample, the output overshot the 21% level, then reversed and undershot the 21% level, and then slowly approached the 21% level asymptotically. It was found that the recovery period required for the output to attain the actual 21% level varied depending both on the duration of exposure to carbon dioxide and the amount of carbon dioxide in the sample. For example, when using such a prior art electrode on an automobile exhaust, an exposure for a period one minute to the exhaust gases resulted in a recovery period on the order of two to three hours before an accurate ambient response could be attained.

This phenomenon is a result of the small volume of electrolyte trapped adjacent to the gold cathode by the porous membrane. This is typically on the order of 1 microliter. As previously mentioned, the response of such a cell is dependent on the pH of the electrolyte. When $CO_2$ is introduced, carbonic acid is formed which, when mixed with such an extremely small volume of basic electrolyte, results in a change of the pH of the electrolyte adjacent the gold cathode. In the typical electrolyte having a pH of approximately 13.5, the introduction of carbonic acid having a pH in the order of 4.5 results in a change of pH of the electrolyte trapped adjacent the gold cathode to a level of approximately 9. The response of the electrode will be correspondingly reduced until such time as the pH can attain its normal value by diffusion of normal electrolyte into the space between the membrane. The initial overshoot observed is, presumably, caused by the sudden change in pH and the unsettling of the electrolyte in the cathode area.

Attempts at improving the performance of oxygen electrodes are not new in the art. It is well known that changes in pH of the electrolyte adjacent the cathode will change the response of the electrode. On the other hand, it is known that the thickness of the electrolyte in this same area affects the sensitivity of the electrode to oxygen. Thus, ideally, the spacing between the membrane and the cathode is kept minimal while means are provided for allowing the free movement of the electrolyte through the space. Thus, in the prior art, it has been suggested to roughen the surface of the gold cathode, provide channels therein for the movement of electrolyte, and depose porous materials between the membrane and the cathode to provide channels for the movement of the electrolyte.

Such prior art suggestions have resulted in oxygen electrodes of marginal sensitivity and poor response times for certain applications. In particular, automobile exhaust analysis and flue gas analysis provide environments imposing restrictions beyond the capabilities of prior art $O_2$ electrodes employing such techniques. In the field of automobile exhaust gas analysis, the ability to cycle and recover at rapid rates is imperative in "assembly line" type testing environments.

Therefore, it is the object of the present invention to provide an oxygen electrode which is sensitive to the partial pressure of oxygen to a degree allowing it to be satisfactorily employed in critical applications such as automobile exhaust gas analysis and flue gas analysis while at the same time having a virtually instantaneous recovery rate following exposure to high levels of carbon dioxide concentration.

SUMMARY

The foregoing objective has been achieved in the preferred embodiment of the present invention by providing an oxygen electrode having an improved electrolyte coupled with a porous layer of between 0.002 and 0.010 inches disposed between the membrane and the gold cathode. The improved electrolyte consists of a solution of KCl containing from 0.1 to 2% KOH. In the preferred embodiment, 0.5% KOH is contained in a 5% KCl solution. This unique combination of a particularly beneficial membrane spacing and an improved electrolyte allows the construction of an $O_2$ electrode which can be cycled between an oxygen bearing atmosphere and 100% $CO_2$ without interference from the $CO_2$. In an alternative embodiment the improved electrolyte is combined with a porous gold cathode to allow electrolyte interchange through the cathode.

DESCRIPTION OF THE PREFERRED EMBODIMENT

Figure 1:
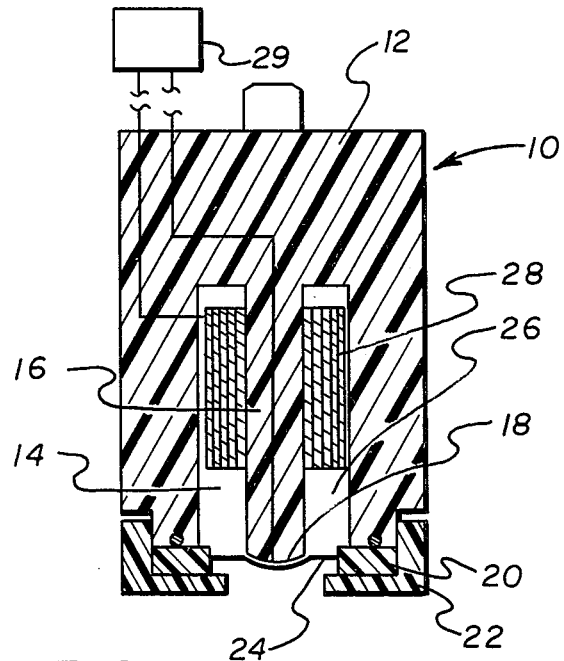
FIG. 1 is a cross section through an electrode according to the prior art.
Figure 4:
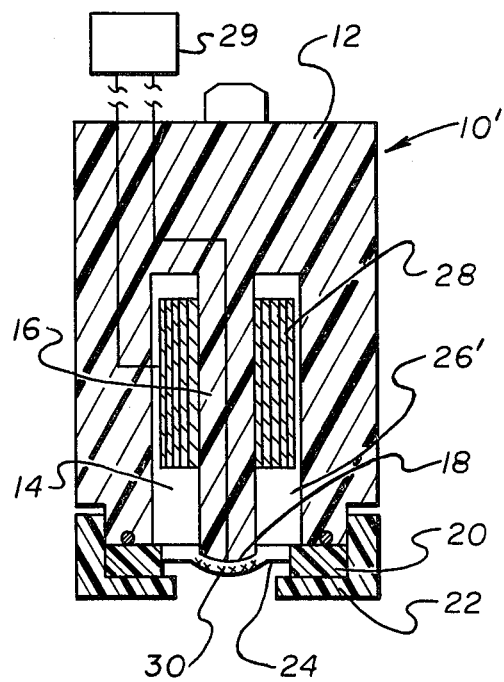
FIG. 4 is a cross section through an electrode according to the preferred embodiment of the present invention.

Referring to FIG. 4, the preferred embodiment of the present invention is shown as an electrode, generally indicated as 10', substantially in accordance with that of FIG. 1 with corresponding parts identified with like numbers. To achieve the objective of the present invention, it is first necessary to dispose an extremely wettable material such as paper or glass fiber paper as a spacer 30 between the gold cathode 18 and the membrane 24. The spacer 30 provides a volume for the electrolyte 26' which can interchange with the main volume of electrolyte to maintain a constant pH as a sample containing high levels of $CO_2$ is exposed to the sensor. It is preferred that glass fiber paper be used being a minimum of 0.002 inches thick and a maximum of 0.010 inches thick with 0.003 inches thickness being preferred and providing superior results. Glass fiber papers thicker than 0.010 inches cause a corresponding decrease in the response time of the electrode beyond that which is acceptable. Thicknesses less than 0.002 inches do not provide sufficient volume of electrolyte for satisfactory operation. Second, in addition to the spacer 30, the electrolyte 26' is composed of a KCl solution less than the saturation level, with 5% KCl being preferred. To this is added from 0.1 to 2% KOH with 0.5% being preferred. Higher levels of KOH were found to attenuate the response due to $O_2$. The improved cell 10' combining the preferred 0.003 inch spacer 30 and the improved electrolyte containing 5% KCl and 0.5% KOH was found to perform without any appreciable change in the span when the electrode was continuously cycled between 100% $CO_2$ and air samples with a potential of 750 millivolts applied between the cathode and anode by means 29.

Figure 5:
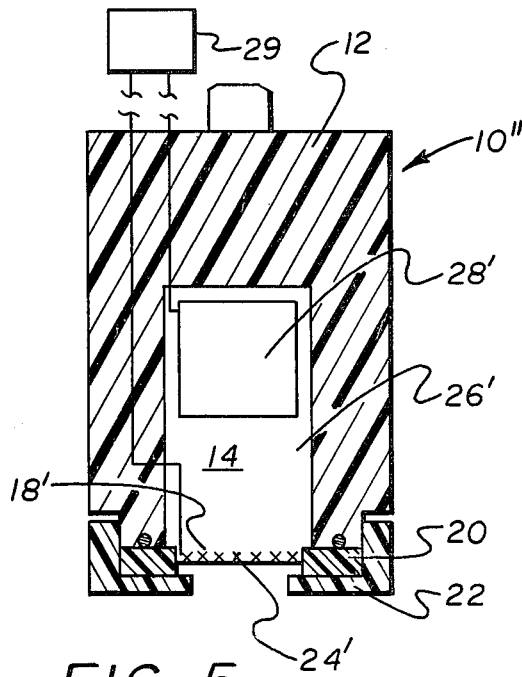
FIG. 5 is a cross section through an electrode according to an alternate embodiment of the present invention.
Figure 2:
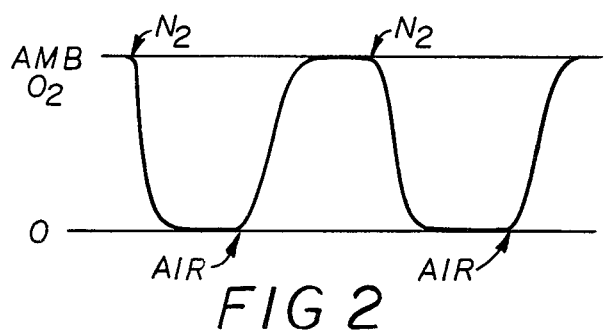
FIG. 2 is an illustration of the output of a prior art electrode when cycled between nitrogen and ambient air.
Figure 3:
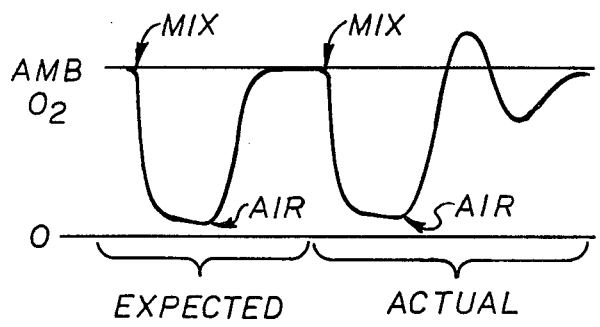
FIG. 3 is a drawing of the output, both expected and actual, of a prior art electrode being cycled between a mixture containing $CO_2$ and ambient air.

An alternate embodiment is shown in FIG. 5. In this embodiment, generally labeled 10'', the body 12 having enclosure 14 therein no longer is provided with cathode support 16. An improved porous gold cathode 18' is combined with the membrane 24' and disposed over the opening to enclosure 14. The gold cathode 18' is formed by pressing 300 mesh gold powder over a gold screen between 42 and 300 mesh. Electrode 18' is loosely covered with a 0.0005 inch polytetrafluoroethylene membrane 24'. The anode 28' is formed either from a silver foil or is another gold screen electrode as described above that is three to four times larger in area compared to the cathode 18'. The electrolyte 26' employed, again consists of a KCl solution containing from 0.1 to 5% KOH with 0.5% being preferred. In this embodiment, the means for interchange of electrolyte 26' between that disposed between the cathode 18' and the membrane 24' and the main volume of electrolyte is the porosity of the cathode itself. Rather than moving radially to interchange at the edges of the cathode as in the preferred embodiment, the electrolyte can interchange throughout the entire cathode area. The main limitation of this alternate embodiment is, of course, the cost of the gold employed therein. When employing a gold electrode as the anode 28', which is preferred in this alternate embodiment, it is highly desirable that the gold anode not be exposed to the ambient air (containing $O_2$) due to leaks in the construction as the anode will also respond to $O_2$ thus injecting an offsetting error signal. When employing the alternate embodiment of FIG. 5, a potential of up to 900 millivolts may be applied to the electrodes by means 29.

While the techniques described herein as comprising the present invention have employed electrodes made from gold and silver, any electrode pair adaptable for oxygen measurement, whether of a noble metal or other material, could equally be used with attendant benefits.

Having thus described our invention, we claim:

1. An improved polarographic oxygen electrode comprising:
   (a) a body having an enclosure therein and an opening into said enclosure;
   (b) a noble metal anode disposed within said enclosure;
   (c) a porous membrane disposed across said opening;
   (d) an electrolyte disposed within said enclosure, said electrolyte being a solution containing KCl at less than saturation and KOH at between 0.1 and 2.0 percent;
   (e) a gold cathode assembly disposed within said enclosure adjacent said membrane and including means for said electrolyte to interchange between a portion of said electrolyte disposed between said cathode and said membrane and the remainder of said electrolyte; and,
   (f) means for applying an electrical potential across said anode and said cathode.

2. The improved electrode of claim 1 wherein: said gold cathode is spaced 0.003 inches from said membrane.

3. The improved electrode of claim 2 wherein: said electrolyte contains at least 5 percent KCl and contains 0.5 percent KOH.

4. The improved electrode of claim 1 wherein said electrolyte interchange means comprises:

a wettable material disposed between said cathode and said membrane.

5. The improved electrode of claim 4 wherein:
said wettable material is 0.003 inch thick glass fiber paper.

6. The improved electrode of claim 1 wherein:
(a) said electrolyte interchange means is a porous cathode comprised of gold screen having gold powder pressed therein; and,
(b) said anode is between 3 and 4 times larger in area as compared to said cathode.

7. The improved electrode of claim 6 wherein:
said anode is comprised of gold screen having gold powder pressed therein.

8. The improved electrode of claim 7 wherein:
(a) said gold screen is between 42 and 300 mesh; and,
(b) said gold powder is 300 mesh.

9. An improved polarographic oxygen electrode of the type having a body with an enclosure therein and an opening into the enclosure, an anode in the enclosure, a porous membrane across the opening, a gold cathode within the enclosure adjacent the membrane, and a KCl electrolyte filling the enclosure, the improvement comprising:
(a) means for the electrolyte to move into and out of the space between the gold cathode and the membrane whereby the electrolyte in said space is maintained at a substantially constant pH value; and,
(b) the electrolyte containing between 0.1 and 2.0 percent KOH.

10. The improved electrode of claim 9 wherein said means for electrolyte movement comprises:
a glass fiber paper spacer between 0.002 and 0.010 inches thick disposed between the cathode and the membrane.

11. The improved electrode of claim 10 wherein:
(a) said spacer is 0.003 inches thick; and,
(b) said KOH is in the amount of 0.5 percent.

12. The improved electrode of claim 9 wherein:
said means for electrolyte movement comprises pores disposed in the cathode whereby electrolyte can pass through the cathode.

13. The improved electrode of claim 12 wherein:
the cathode is comprised of gold screen having gold powder pressed therein.

* * * * *